(12) United States Patent
Nakaminami et al.

(10) Patent No.: US 7,960,132 B2
(45) Date of Patent: Jun. 14, 2011

(54) MEASURING DEVICE, MEASURING APPARATUS, AND MEASURING METHOD

(75) Inventors: Takahiro Nakaminami, Osaka (JP); Jin Muraoka, Osaka (JP)

(73) Assignee: Panasonic Corporation, Osaka (JP)

( * ) Notice: Subject to any disclaimer, the term of this patent is extended or adjusted under 35 U.S.C. 154(b) by 3 days.

(21) Appl. No.: 12/389,997

(22) Filed: Feb. 20, 2009

(65) Prior Publication Data

US 2009/0162879 A1 Jun. 25, 2009

Related U.S. Application Data

(63) Continuation of application No. PCT/JP2007/065637, filed on Aug. 9, 2007.

(30) Foreign Application Priority Data

Aug. 21, 2006 (JP) ................... 2006-223800

(51) Int. Cl.
    C12Q 1/58 (2006.01)
    G01N 33/53 (2006.01)
    G01N 21/00 (2006.01)

(52) U.S. Cl. ............. 435/7.6; 435/7.1; 435/12; 435/7.8; 436/164

(58) Field of Classification Search ........................ None
    See application file for complete search history.

(56) References Cited

U.S. PATENT DOCUMENTS

| | | | |
|---|---|---|---|
| 4,427,781 A | | 1/1984 | Masson et al. |
| 4,665,034 A | * | 5/1987 | Chandler ................ 435/287.2 |
| 6,824,985 B1 | | 11/2004 | Rheinheimer et al. |
| 2004/0157281 A1 | | 8/2004 | Hulkower et al. |

FOREIGN PATENT DOCUMENTS

| | | |
|---|---|---|
| EP | 1739407 | 1/2007 |
| JP | 03-046566 | 2/1991 |
| JP | 05-000665 | 1/1993 |
| JP | 07-248310 | 9/1995 |
| JP | 09-127126 | 5/1997 |
| JP | 11-133023 | 5/1999 |
| JP | 2002-509247 | 3/2002 |
| JP | 2005-230625 | 9/2005 |
| JP | 2005-315593 | 11/2005 |
| JP | 2005-345464 | 12/2005 |
| WO | WO 99/36765 | 7/1999 |

OTHER PUBLICATIONS

Annual Report of the Medical Research Institute, Kanazawa Medical University, 1999, pp. 137-146, vol. 10.
European Search Report issued in European Patent Application No. 07 79 2287, dated Nov. 5, 2009.
Full English Translation of Annual Report of the Medical Research Institute: Chemical Diagnosis of Biotin Deficiency in two Japanese Infants Fed with Amino Acid Formula Using GC/MS, Kanazawa Medical University, 1999, vol. 10, pp. 137-146.

* cited by examiner

*Primary Examiner* — Rebecca Prouty
*Assistant Examiner* — Paul Martin
(74) *Attorney, Agent, or Firm* — McDermott Will & Emery LLP

(57) ABSTRACT

A measuring device (100*a*) includes a base body (101) constituting: a sample holding portion (102) configured to hold a test sample containing urea and a material to be detected; and a sample supply port (103) through which the test sample is supplied to the sample holding portion (102). The base body includes an optical measuring portion and a reagent holding portion (111) which are configured to carry out an optical measurement of the test sample held by the sample holding portion (102). The reagent holding portion holds an antibody to the material to be detected and urease which causes hydrolysis of the urea. With this, the present invention provides a measuring device, a measuring apparatus, and a measuring method, each having a simple configuration and capable of reducing measurement errors caused by the urea contained in the test sample and accurately measuring the material to be detected.

2 Claims, 10 Drawing Sheets

MEASURING DEVICE, MEASURING APPARATUS, AND MEASURING METHOD

This Application is a continuation of International Application No. PCT/JP2007/065637, whose international filing date is Aug. 9, 2007 which in turn claims the benefit of Japanese Patent Application No. 2006-223800, filed on Aug. 21, 2006, the disclosures of which Applications are incorporated by reference herein. The benefit of the filing and priority dates of the International and Japanese Applications is respectfully requested.

TECHNICAL FIELD

The present invention relates to a measuring device, a measuring apparatus, and a measuring method, each designed to measure a material to be detected which is contained in a test sample containing urine.

BACKGROUND ART

POCT (Point Of Care Testing) units have been used in a field of clinical examinations as measuring units required for quick and accurate diagnoses and treatments in front of patients.

Examples of the POCT unit are a blood sugar sensor, a pregnancy diagnosis device, an ovulation test device, and a HbA1c/microalbumin creatinine measuring apparatus (for example, DCA2000 System produced by Bayer Medical Ltd.). Since the POCT units can focus on a marker material specific to a certain clinical condition to easily and quickly measure the marker material, they are very effective for screening and monitoring of a subject being tested. In addition, since the POCT units are comparatively small, they excel in portability and can be introduced at low cost. Further, since the POCT units do not require special expertise for operating them, they have the advantage that anyone can easily use them.

The POCT unit normally means a measuring unit used for clinical examinations in medical practice except for examination rooms of hospitals and examination centers. In recent years, the POCT units are widely used in home medical care practice because of their excellent portability, economical efficiency, and operability. Therefore, in recent years, the POCT unit means not only a measuring unit used for clinical examinations in medical practice except for examination rooms of hospitals and examination centers but also a measuring unit used in home medical care practice (see Patent Documents 1 and 2 for example).

At present, in the clinical examination, there are a large number of measurement items for accurate diagnosis and treatment of a disease of a patient. For example, for accurate diagnosis and treatment of diabetes, HbA1c, albumin, insulin, C-peptide, ketone body, and the like are set as materials to be detected in the clinical examination. In a case where a test sample is a body fluid, such as urine, major examples of a measuring method for measuring these materials to be detected are an optical measuring method and an electrochemical measuring method. By using any one of these measuring methods, the POCT units and conventional large-scale automatic measuring units measure the material to be detected which is contained in the test sample.

A conventional optical measuring method is a measuring method for measuring the material to be detected which is contained in the test sample based on optical changes. Therefore, in a case where the amount of the material to be detected which was contained in the test sample was extremely small, the measurement of the material to be detected was not accurately carried out in some cases. Moreover, in the case of using the conventional optical measuring method, a special component needs to be prepared which accurately measures the extremely small amount of the material to be detected which is contained in the test sample. Therefore, the measuring unit was not provided at a low price in some cases.

Here, disclosed as the optical measuring method capable of accurately measuring the material to be detected which is contained in the test sample without preparing the special component is an optical measuring method for generating aggregate containing the material to be detected in the test sample to measure the material to be detected based on a turbidity level of the test sample which is turbid due to the aggregate (see Patent Document 3 for example).

According to the optical measuring method disclosed as above, when carrying out the clinical examination, the urine as the test sample containing albumin (antigen) as the material to be detected and a mixture of an anti-albumin antibody (antibody) and polyethylene glycol that is an agglutination promoter are mixed with each other. Thus, in the urine as the test sample, the aggregate (to be specific, antigen-antibody aggregate) of the albumin as the material to be detected and the anti-albumin antibody is generated. Then, in this optical measuring method, the turbidity level of the test sample which is turbid due to the antigen-antibody aggregate is measured by a turbidimetric determination using light of a wavelength of 470 nm. Thus, the measurement (quantitation) of the albumin as the material to be detected which is contained in urine that is the test sample is carried out.

Patent Document 1: Japanese Laid-Open Patent Application Publication No. Hei. 7-248310

Patent Document 2: Japanese Laid-Open Patent Application Publication No. Hei. 3-046566

Patent Document 3: Published Japanese Translation of PCT Application No. 2002-509247

DISCLOSURE OF THE INVENTION

Problems to be Solved by the Invention

However, the inventors of the present application have found the problem that in the optical measuring method disclosed as above, the amount of the antigen-antibody aggregate generated in the urine that is the test sample changes depending on the concentration of urea contained in the urine. To be specific, the inventors of the present application have found that even in the case of using the optical measuring method disclosed as above, the turbidity level of the test sample changes depending on the concentration of the urea contained in the urine, so that it is still impossible to provide at a low price the POCT unit capable of accurately measuring the material to be detected which is contained in the test sample.

The present invention was made to solve the above conventional problem, and an object of the present invention is to provide a measuring device, a measuring apparatus, and a measuring method, each having a simple configuration and capable of reducing measurement errors caused by the urea contained in the test sample and accurately measuring the material to be detected.

Means for Solving the Problems

To solve the above conventional problems, a measuring device according to the present invention includes a base body constituting: a sample holding portion configured to hold a test sample containing urea and a material to be detected; and a sample supply port through which the test sample is supplied to the sample holding portion, wherein: the base body includes an optical measuring portion and a reagent holding portion which are configured to carry out an optical measurement of the test sample held by the sample holding portion; and the reagent holding portion holds an antibody to the material to be detected and urease which causes hydrolysis of the urea.

With this configuration, since the reagent holding portion holds the urease which causes the hydrolysis of the urea contained in the test sample, it is possible to solve the problem that the amount of antigen-antibody aggregate generated in the test sample changes depending on the concentration of the urea. Therefore, it is possible to provide the measuring device having a simple configuration and capable of reducing measurement errors caused by the urea contained in the test sample and accurately measuring the material to be detected.

In this case, the sample holding portion is a space formed inside the base body so as to be communicated with the sample supply port, and the reagent holding portion is formed on an inner surface of the space such that the antibody and the urease are exposed to the space.

With this configuration, since the sample holding portion is the space formed inside the base body so as to be communicated with the sample supply port, the sample holding portion can surely hold the test sample supplied from the sample supply port. Moreover, since the reagent holding portion is formed on the inner surface of the space that is the sample holding portion such that the antibody and the urease are exposed to the space, the antibody and the urease can be surely dissolved in the test sample.

Moreover, in the above case, the reagent holding portion holds the antibody and the urease as a complex of the antibody and the urease.

With this configuration, since the reagent holding portion holds the antibody and the urease in the sample holding portion as the complex of the antibody and the urease, it is possible to surely solve the problem that the amount of the antigen-antibody aggregate generated in the test sample changes depending on the concentration of the urea.

Moreover, in the above case, the reagent holding portion holds the antibody and the urease as separate materials.

With this configuration, since the reagent holding portion holds the antibody and the urease in the sample holding portion as separate materials, it is possible to surely solve the problem that the amount of the antigen-antibody aggregate generated in the test sample changes depending out the concentration of the urea, without preparing the complex of the antibody and the urease.

Moreover, in the above case, the optical measuring portion includes: a light incident portion configured to allow light to be incident from an outside of the sample holding portion to an inside of the sample holding portion; and a light emanating portion configured to allow the light to be emanated from the inside of the sample holding portion to the outside of the sample holding portion.

With this configuration, since the optical measuring portion includes the light incident portion and the light emanating portion, it is possible to easily carry out the optical measurement (turbidimetric determination) of the test sample held by the sample holding portion.

Meanwhile, a measuring apparatus according to the present invention includes: a measuring device attaching portion to which the characteristic measuring device according to the present invention is attached; a light source configured to emit light incident on the optical measuring portion of the measuring device attached to the measuring device attaching portion; a light receiving portion configured to receive the light emanated from the optical measuring portion of the measuring device attached to the measuring device attaching portion; and a calculating portion configured to detect or quantitate the material to be detected which is contained in the test sample, based on the emanated light received by the light receiving portion.

With this configuration, since the reagent holding portion includes the measuring device attaching portion to which the measuring device holding the antibody and the urease is attached, it is possible to provide the measuring apparatus having a simple configuration and capable of reducing the measurement errors caused by the urea contained in the test sample and accurately measuring the material to be detected.

In this case, the measuring apparatus further includes a suction portion configured to suction the test sample to the sample holding portion of the measuring device attached to the measuring device attaching portion.

With this configuration, since the measuring apparatus further includes the suction portion, it is possible to easily suction the test sample to the sample holding portion of the measuring device attached to the measuring device attaching portion.

Then, a measuring method according to the present invention is a measuring method using a measuring device including: a sample holding portion configured to hold a test sample containing urea and a material to be detected; and an optical measuring portion and a reagent holding portion which are configured to carry out an optical measurement of the test sample held by the sample holding portion, the reagent holding portion holding an antibody to the material to be detected and urease which causes hydrolysis of the urea, the measuring method comprising the steps of: (A) introducing the test sample to the sample holding portion of the measuring device to cause the hydrolysis of the urea contained in the test sample by the urease and to generate an aggregate of the material to be detected which is contained in the test sample and the antibody; (B) causing light emitted from a light source to be incident on the optical measuring portion of the measuring device and causing the light emanated from the optical measuring portion of the measuring device to be incident on a light receiving element; and (C) detecting or quantitating the material to be detected which is contained in the test sample, based on the light received by the light receiving element in the step (B).

With this configuration, since the measuring method using the measuring device includes the steps (A) to (C), it is possible to solve the problem that the amount of the antigen-antibody aggregate generated in the test sample changes depending on the concentration of the urea. Thus, it is possible to provide the measuring method having a simple configuration and capable of reducing the measurement errors caused by the urea contained in the test sample and accurately measuring the material to be detected.

In this case, the step (A) includes the steps of: (D) immersing the measuring device in the test sample; and (E) suctioning the test sample to the sample holding portion of the measuring device.

With this configuration, since the step (A) includes the step (D) of immersing the measuring device in the test sample and the step (E) of suctioning the test sample to the sample holding portion of the measuring device, it is possible to easily introduce the test sample to the sample holding portion of the measuring device.

EFFECTS OF THE INVENTION

In accordance with the above characteristic configuration according to the present invention, it is possible to provide a measuring device, a measuring apparatus, and a measuring method, each having a simple configuration and capable of reducing the measurement errors caused by the urea contained in the test sample and accurately measuring the material to be detected.

Figure 1:
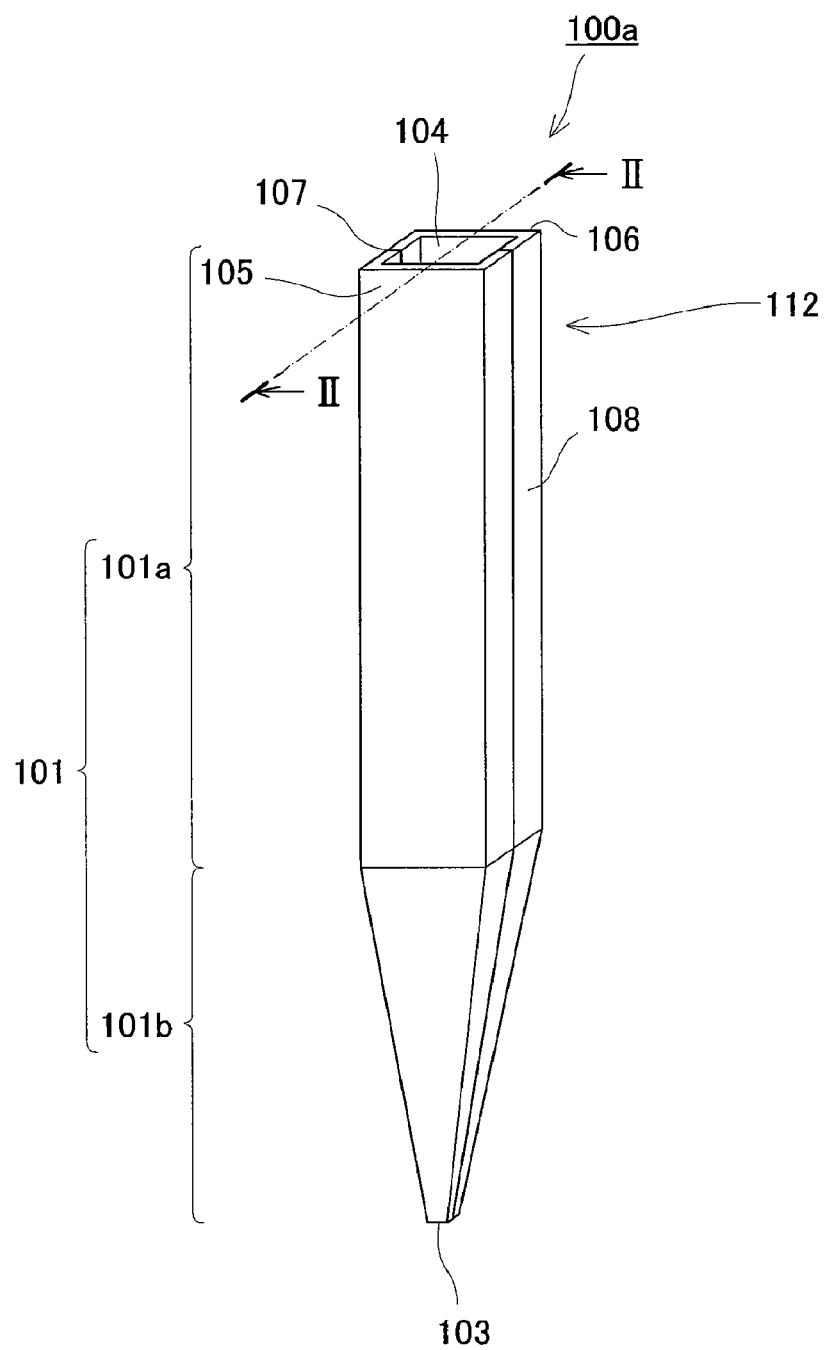
FIG. 1 is a perspective view schematically showing the configuration of a measuring device according to Embodiment 1 of the present invention.

EXPLANATION OF REFERENCE NUMBERS 100a, 100b measuring device
101 base body
101a hollow quadrangular prism portion
101b hollow quadrangular pyramid portion
102 sample holding portion
103 sample supply port
104 suction port
105 first surface
106 fourth surface
107 second surface (light incident portion)
108 third surface (light emanating portion)
109 first reagent holding portion
110 second reagent holding portion
111 reagent holding portion
112 optical measuring portion
201 first member
202 second member
300 measuring apparatus
301 measuring device attaching portion
302 display portion
303 sample suction start button
304 measuring device detach button
401 controller
404 piston mechanism
406 timer portion
407 light source
408 photoreceiver
409 memory
410 measuring device detach mechanism
411 recording portion
412 transmitting portion
413 receiving portion
500 urease-antibody complex
500a urease
500b glutaraldehyde
500c antibody

BEST MODE FOR CARRYING OUT THE INVENTION

Hereinafter, the best mode for carrying out the present invention will be explained in detail in reference to the drawings.

Embodiment 1

Embodiment 1 of the present invention will explain a case where a test sample is urine, and a material to be detected is human albumin.

First, the configuration of a measuring device according to Embodiment 1 of the present invention will be explained in detail in reference to FIGS. 1 and 2.

FIG. 1 is a perspective view schematically showing the configuration of the measuring device according to the present embodiment. FIG. 2 is a cross-sectional view schematically showing the configuration of a cross section taken along line II-II of the measuring device shown in FIG. 1.

In the present embodiment, a base body 101 constituting a measuring device 100a is the same in configuration as a base body of a conventional measuring device.

Figure 2:
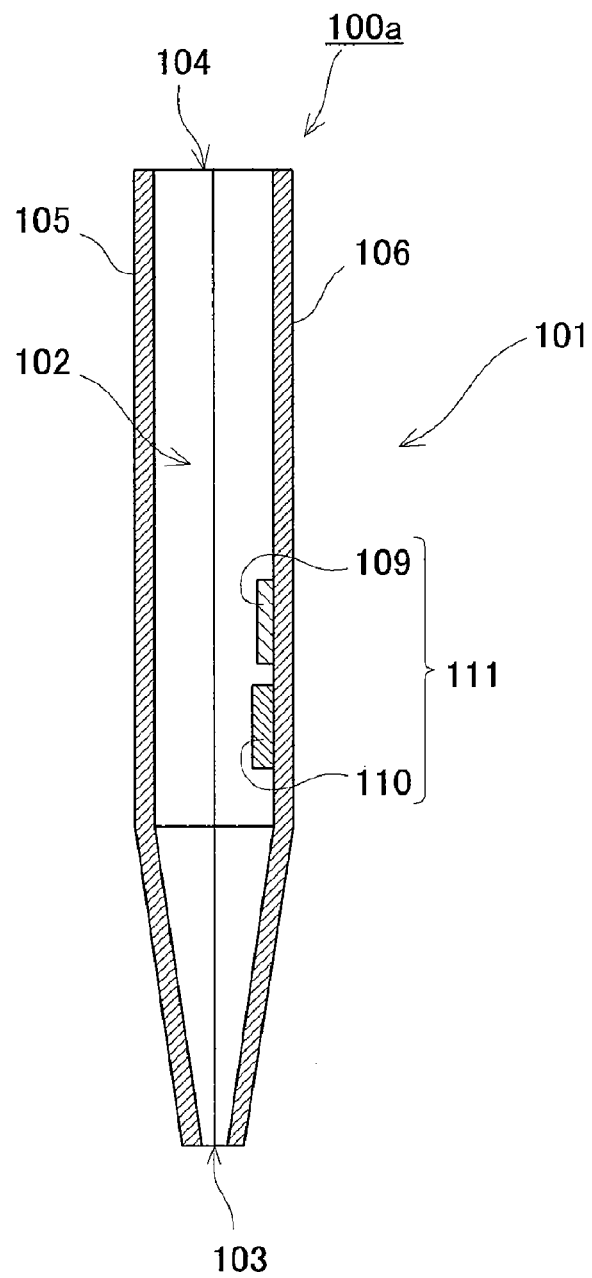
FIG. 2 is a cross-sectional view schematically showing the configuration of a cross section taken along line II-II of the measuring device shown in FIG. 1.

To be specific, as shown in FIGS. 1 and 2, the measuring device 100a according to the present embodiment includes the base body 101 which is made of transparent polystyrene and is hollow. Both end portions of the base body 101 are cut in a lateral direction to open to the outside. A space is formed inside the base body 101, and serves as a sample holding portion 102 of the measuring device 100a.

One open end portion of the space serving as the sample holding portion 102 serves as a sample supply port 103, and the other open end portion of the space serves as a suction port 104. More specifically, the base body 101 includes a hollow quadrangular prism portion 101a and a hollow quadrangular pyramid portion 101b. The suction port 104 is formed at one end portion of the hollow quadrangular prism portion 101a, and the hollow quadrangular pyramid portion 101b is formed integrally with the other end portion of the hollow quadrangular prism portion 101a. The sample supply port 103 is formed at one end portion of the hollow quadrangular pyramid portion 101b which end portion is opposite an end portion contacting the hollow quadrangular prism portion 101a. In the present embodiment, as will be described later, after a part of the measuring device 100a is immersed in the urine stored in a container for example, air inside the sample holding portion 102 is suctioned from the suction port 104 by a piston mechanism 404 of a measuring apparatus 300, and thus, the urine is supplied to the sample holding portion 102.

In the present embodiment, among four surfaces constituting an outer surface of the hollow quadrangular prism portion 101a, a second surface 107 located at a position sandwiched between a first surface 105 and a fourth surface 106 serves as a light incident portion (hereinafter also referred to as "light incident portion 107"). Moreover, in the present embodiment, among four surfaces constituting the outer surface of the hollow quadrangular prism portion 101a, a third surface 108 which is located at a position sandwiched between the first surface 105 and the fourth surface 106 and is opposed to the second surface 107 serves as a light emanating portion (hereinafter also referred to as "light emanating portion 108"). In the present embodiment, the second surface (light incident portion) 107 and the third surface (light emanating portion) 108 constitute an optical measuring portion 112 configured to carry out an optical measurement of the test sample held by the sample holding portion 102.

As shown in FIG. 2, in the measuring device 100a according to the present embodiment, a first reagent holding portion 109 and a second reagent holding portion 110 are disposed on an inner wall surface of the fourth surface 106 of the hollow quadrangular prism portion 101a, among inner wall surfaces surrounding the sample holding portion 102. Here, each of the first reagent holding portion 109 and the second reagent holding portion 110 is disposed to have a portion exposed to the space that is the sample holding portion 102.

As above, the measuring device 100a according to the present embodiment includes the base body 101 which is hollow, and the sample holding portion 102 which holds the test sample containing the urea and the material to be detected is formed inside the base body 101. Moreover, the measuring device 100a includes the sample supply port 103 and the suction port 104 which are communicated with the sample holding portion 102, and the optical measuring portion 112 configured to carry out the optical measurement of the test sample. Further, the measuring device 100a includes a reagent holding portion 111 at a predetermined position of the inner wall surface of the base body 101, and the reagent holding portion 111 holds an antibody to the material to be detected and urease.

With this configuration, only by using one measuring device 100a and supplying the test sample to the sample holding portion 102 once, the generation of aggregate by an antigen-antibody reaction and the hydrolysis of the urea by the urease can be realized. To be specific, by dissolving of the urease held by the reagent holding portion 111 in the test sample, the hydrolysis reaction of the urea by the urease proceeds as shown by Chemical Formula 1, so that the concentration of the urea contained in the test sample decreases. Then, by causing light to be incident on the optical measuring portion 112 of the measuring device 100a to measure scattered light and transmitted light emanated from the optical measuring portion 112 of the measuring device 100a, it is possible to accurately measure the amount of the aggregate generated. Therefore, with this simple configuration, measurement errors caused by the urea contained in the test sample can be reduced, and the antigen that is the material to be detected can be accurately measured.

Chemical Formula 1

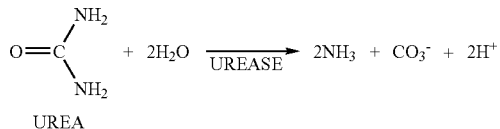

UREA

Moreover, in the measuring device 100a according to the present embodiment, the optical measuring portion 112 includes: the light incident portion 107 configured to allow the light to be incident from an outside of the sample holding portion 102 to an inside of the sample holding portion 102; and the light emanating portion 108 configured to allow the light to be emanated from the inside of the sample holding portion 102 to the outside of the sample holding portion 102.

Here, it is preferable that the light incident portion 107 and the light emanating portion 108 be formed by an optically transparent material or a material which does not practically absorb visible light. Examples of such material are quartz, glass, polystyrene, and polymethylmethacrylate. Especially, in a case where the measuring device 100a is formed as a disposable type, it is preferable that the light incident portion 107 and the light emanating portion 108 be formed by polystyrene from the standpoint of cost.

Moreover, in the measuring device 100a according to the present embodiment, the reagent holding portion 111 includes the first reagent holding portion 109 and the second reagent holding portion 110. Then, it is preferable that the first reagent holding portion 109 hold the antibody, and the second reagent holding portion 110 hold the urease. With this, dissolving of the antibody and the urease in the test sample becomes further smooth as compared to a case where the antibody and the urease are mixed with each other and dried, and the dried mixture is held by the same reagent holding portion. Therefore, the optical measurement of the test sample can be stably carried out.

In the measuring device 100a according to the present embodiment, it is preferable that reagents, such as the antibody and the urease, be held inside the sample holding portion 102 in a dry state, and be disposed to be easily dissolved in the test sample when the test sample is supplied to the sample holding portion 102. For example, a porous carrier made of glass fiber, filter paper, or the like is immersed in a solution of the reagent, and then is dried. Thus, the reagent, such as the antibody or the urease, is supported by the carrier. Then, the carrier supporting the reagent may be disposed in the sample holding portion 102. Or, the solution of the reagent is directly applied to a part of the inner wall surface constituting the sample holding portion 102, and is adequately dried. Thus, the reagent, such as the antibody or the urease, may be disposed in the sample holding portion 102. Or, the reagent may be freeze-dried outside the sample holding portion 102, and the freeze-dried reagent may be disposed inside the sample holding portion 102.

Here, examples of the antibody contained in the reagent are an antibody to protein, such as albumin and CRP, contained in the urine and an antibody to hormone, such as hCG and LH, contained in the urine. Since these antibodies can be produced by known methods, they are advantageous in that the reagent is easily prepared. For example, by immunizing a mouse, a rabbit, or the like using protein, such as albumin or CRP, or hormone, such as hCG or LH, as the antigen, the antibody to the antigen can be easily obtained.

In the present embodiment, to promote a reaction of generating the aggregate by the antigen and the antibody, the reagent holding portion 111 may further hold an agglutination promoter. As a main chain of a chemical structure of the agglutination promoter, for example, a compound, such as polyethylene glycol, can be used. Note that an appropriate molecular weight of the agglutination promoter and an appropriate chemical structure of a side chain of the agglutination promoter may be suitably applied in accordance with the type of an agglutination reaction. For example, by setting the molecular weight of the agglutination promoter to 500 to 10,000, the reaction of generating the aggregate by the antigen and the antibody can be adequately promoted. Moreover, in a case where the reagent holding portion 111 further holds the agglutination promoter, it is preferable that the agglutination promoter coexist with the antibody in the vicinity of the antibody in the sample holding portion 102 of the measuring device 100*a*. With this, the reaction of generating the aggregate by the antigen and the antibody can be further promoted.

In the present embodiment, it is preferable that the measuring device 100*a* be detachably attached to a measuring device attaching portion 301 of the below-described measuring apparatus 300. In addition, it is preferable that the measuring device 100*a* be disposable in order to realize an accurate measurement of the material to be detected which is contained in the test sample.

Next, a method for manufacturing the measuring device according to Embodiment 1 of the present invention will be explained in detail in reference to FIG. 3.

Figure 3:
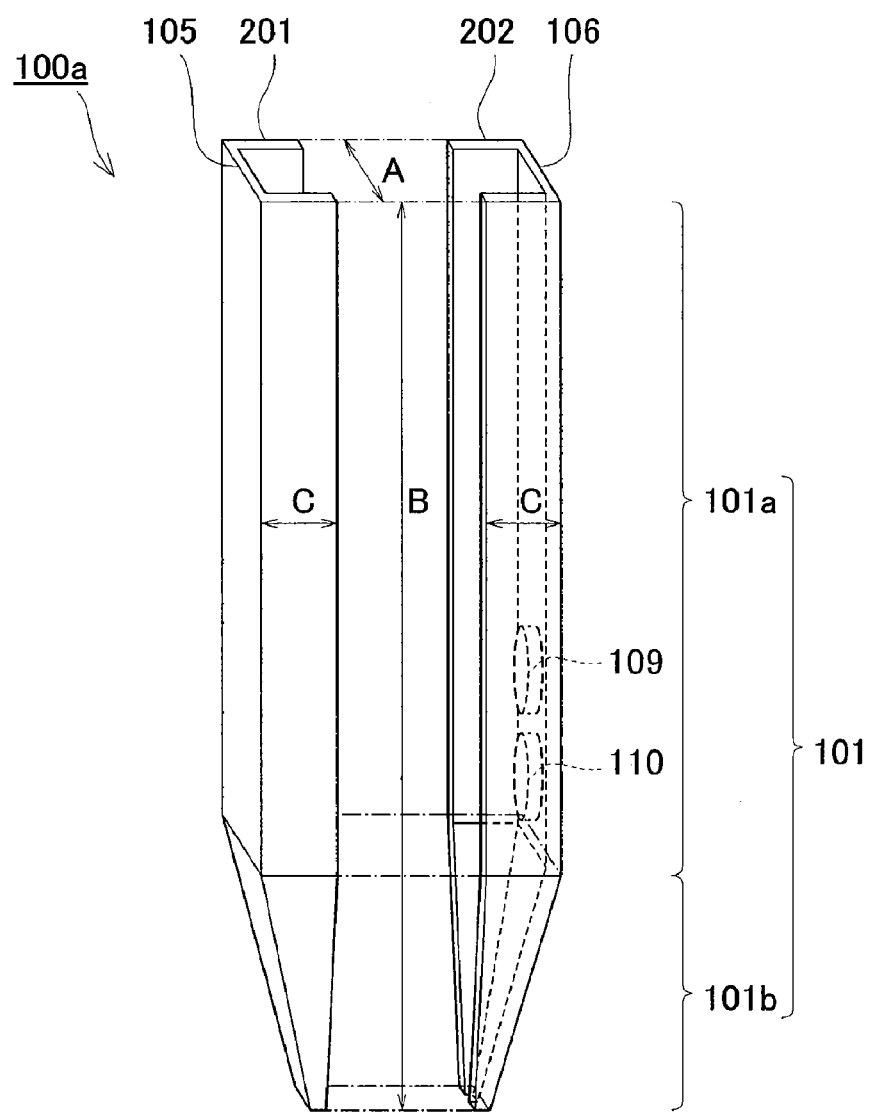
FIG. 3 is an exploded perspective view schematically showing a state where the measuring device according to Embodiment 1 of the present invention is exploded.

FIG. 3 is an exploded perspective view schematically showing a state where the measuring device according to Embodiment 1 of the present invention is exploded.

As shown in FIG. 3, the measuring device 100*a* according to the present embodiment includes a first member 201 and a second member 202. Each of the first member 201 and the second member 202 constituting the measuring device 100*a* is made of transparent polystyrene and has a concave portion. By combining the first member 201 and the second member 202 such that the concave portions thereof face each other, the base body 101 including the hollow quadrangular prism portion 101*a* and the hollow quadrangular pyramid portion 101*b* is formed.

The first member 201 and the second member 202 can be obtained through a molding process using a die. A known resin molding technique may be used as this molding process. Respective sizes of the first member 201 and the second member 202 can be suitably adjusted in accordance with the spec of the measuring device 100*a*, and the like. In the present embodiment, each of the first member 201 and the second member 202 has a width A of 10 mm, a length B of 84 mm, a length C of 6 mm, and a wall portion thickness of 1 mm.

When manufacturing the measuring device 100*a*, the first reagent holding portion 109 and the second reagent holding portion 110 are first formed on the bottom surface of the concave portion of the second member 202, that is, on the inner wall surface of the fourth surface 106.

One example of a method for forming the first reagent holding portion 109 is as follows: A certain amount of an aqueous solution of the antibody to the human albumin that is the reagent used for the optical measurement is applied to be dropped on the bottom surface of the concave portion of the second member 202 by using a micro syringe, or the like, and the second member 202 is placed at about room temperature to 30° C. to evaporate moisture. By this method, it is possible to form the first reagent holding portion 109 which supports an anti-human albumin antibody in a dry state. For example, the first reagent holding portion 109 can be formed as follows: Using the above antibody aqueous solution whose concentration is 8 mg/dL, 0.7 mL of the solution is dropped on a dropped portion whose area is 5 $cm^2$.

Meanwhile, one example of a method for forming the second reagent holding portion 110 is as follows: A certain amount of an aqueous solution of the urease is applied to be dropped using a micro syringe, or the like on a position of the bottom surface of the concave portion of the second member 202 which position is different from a position at which the first reagent holding portion 109 is formed, and the second member 202 is placed at about room temperature to 30° C. to evaporate moisture. By this method, it is possible to form the second reagent holding portion 110 which supports the urease in a dry state. For example, the second reagent holding portion 110 can be formed as follows: Using the urease aqueous solution whose concentration is 476 U/mL, 0.7 mL of the solution is dropped on the dropped portion whose area is 5 $cm^2$. Since a typical activity of the urease is 600 U/mg (for example, in the case of the urease produced by Sigma Co., Ltd.), the concentration of 476 U/mL corresponds to about 0.79 mg/mL.

In the present embodiment, as shown in FIGS. 2 and 3, the second reagent holding portion 110 is formed to be located closer to the sample supply port 103 than the first reagent holding portion 109. However, the present embodiment is not limited to this. For example, conversely, the first reagent holding portion 109 may be formed to be located closer to the sample supply port 103 than the second reagent holding portion 110.

In the present embodiment, the first reagent holding portion 109 and the second reagent holding portion 110 are formed at different positions from each other. However, the present embodiment is not limited to this. One reagent holding portion containing both the antibody and the urease may be formed. For example, by dropping the urease aqueous solution on the antibody which has been dropped and dried, the reagent holding portion containing both the antibody and the urease in a mixed state can be formed. Moreover, by dropping and drying a mixture aqueous solution of the antibody and the urease, one reagent holding portion can be formed.

The concentration of the aqueous solution containing the reagent to be applied and the amount of the aqueous solution dropped can be appropriately determined in accordance with characteristics required for the measuring device 100*a* and a spatial limitation of a formation position in the second member 202. Further, the position of the second member 202 at which position the reagent holding portion 101 is formed and the area of the reagent holding portion 101 formed on the second member 202 can be suitably and appropriately determined in view of, for example, the solubility of the reagent in the test sample and the position of the optical measuring portion 112.

As described above, the antibody to the human albumin can be obtained by a known method. For example, antiserum of a rabbit immunized by the human albumin is purified by protein A column chromatography, and is then dialyzed using a dialysis tube. Thus, the anti-human albumin antibody can be obtained.

Next, the first member 201 and the second member 202 obtained as above are joined to each other based on the positional relation shown by the dashed lines in FIG. 3. Thus, the measuring device 100*a* is assembled. At this time, adhesive, such as epoxy resin, is applied to a joined portion of the first member 201 and a joined portion of the second member 202. Then, the first member 201 and the second member 202 are put together, and this assembly is placed to be dried. Thus, the measuring device 100*a* is assembled. Moreover, the measuring device 100*a* may be assembled as follows: The first member 201 and the second member 202 are put together without applying the adhesive, and the joined portion of the first member 201 and the joined portion of the second member 202 are welded by heat or ultrasound using a commercially available welder.

Thus, the characteristic measuring device 100*a* according to the present embodiment shown in FIGS. 1 and 2 can be obtained.

Next, the configuration of the measuring apparatus according to Embodiment 1 of the present invention will be explained in reference to FIGS. 4 and 5. Note that the measuring apparatus itself according to the present embodiment is the same in configuration as a conventionally known measuring apparatus. Therefore, in the following explanation, a detailed explanation of the configuration of the measuring apparatus will be omitted.

Figure 4:
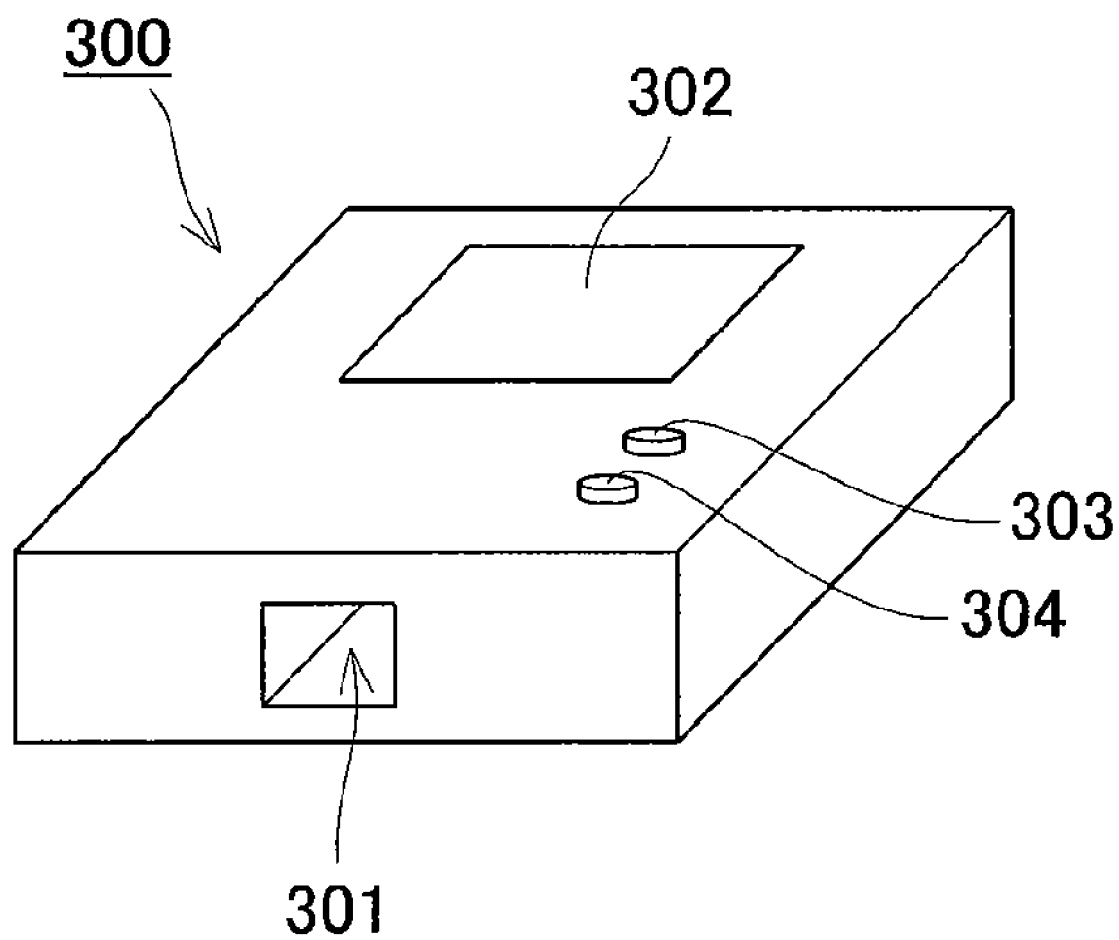
FIG. 4 is a perspective view schematically showing the configuration of a measuring apparatus according to Embodiment 1 of the present invention.

FIG. 4 is a perspective view schematically showing the configuration of the measuring apparatus according to Embodiment 1 of the present invention. FIG. 5 is a block diagram schematically showing an internal configuration of the measuring apparatus according to Embodiment 1 of the present invention.

As shown in FIG. 4, the measuring apparatus 300 according to the present embodiment includes the measuring device attaching portion 301 which allows the measuring device 100a to be attached to the measuring apparatus 300. The measuring device attaching portion 301 is provided with a device attaching port (not shown in FIG. 4) to which the suction port 104 of the measuring device 100a is detachably connected. Moreover, a display portion 302 that is a display which shows measurement results, a sample suction start button 303, and a measuring device detach button 304 are formed on a main surface of the measuring apparatus 300.

A convex portion is formed inside the device attaching port of the measuring apparatus 300. When attaching the measuring device 100a to the measuring apparatus 300, the convex portion is inserted into the suction port 104. Here, it is preferable to improve adhesion between the convex portion and the suction port 104 by disposing, for example, a ring-shaped sealant made of fluorocarbon resin, such as TEFLON, (polytetrafluoroethylene), or elastomeric resin, such as isoprene rubber, around the convex portion formed inside the device attaching port to prevent air leakage from a portion where the measuring device 100a and the measuring apparatus 300 contact each other. Moreover, the convex portion itself may be made of elastomeric resin, such as TEFLON, (polytetrafluoroethylene) or isoprene rubber.

Figure 5:
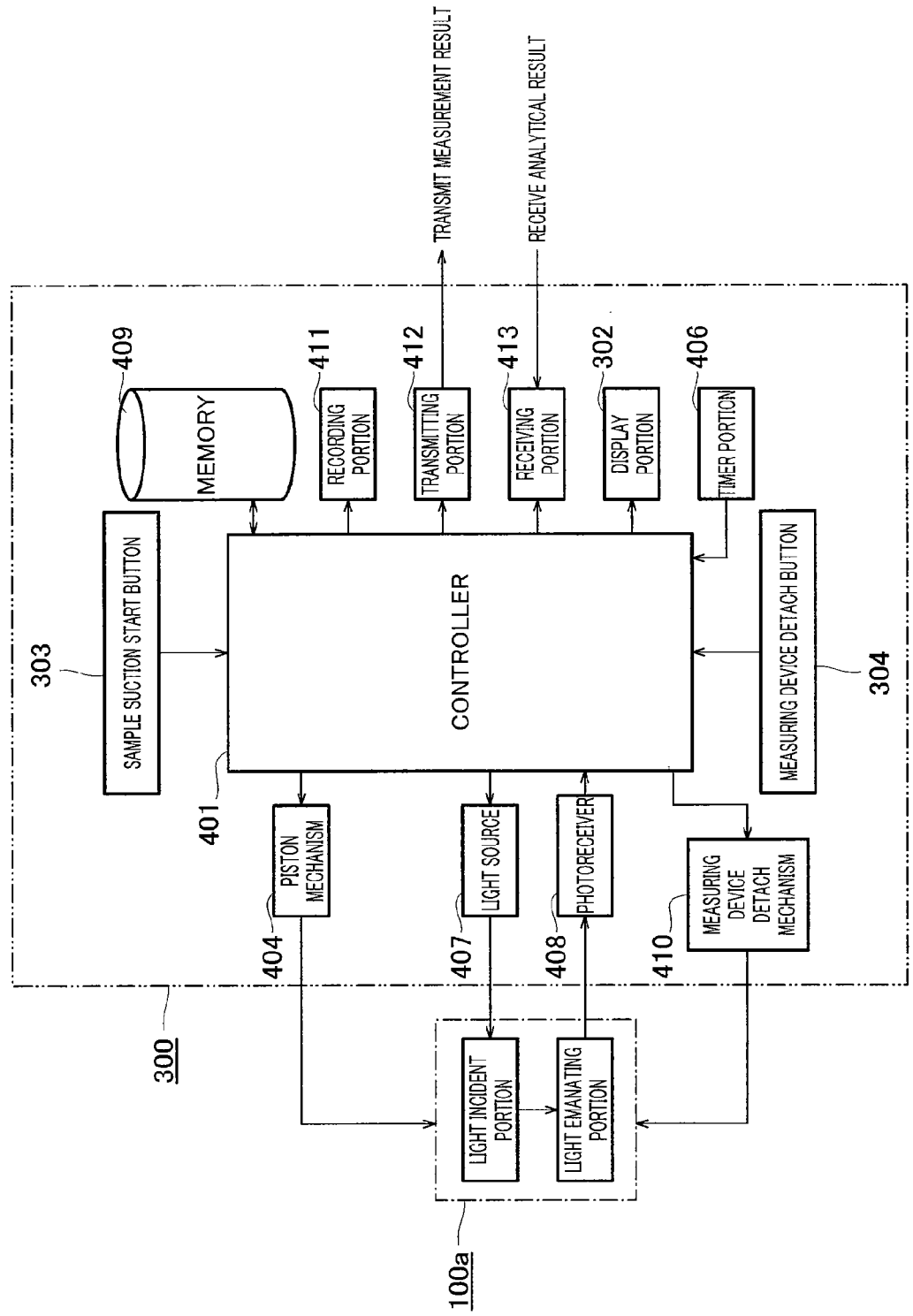
FIG. 5 is a block diagram schematically showing an internal configuration of the measuring apparatus according to Embodiment 1 of the present invention.

As shown in FIG. 5, a light source 407 and a photoreceiver 408 are formed inside the measuring apparatus 300 according to the present embodiment. The light source 407 emits light which is incident on the optical measuring portion 112 of the measuring device 100a attached to the measuring device attaching portion 301, and the photoreceiver 408 is a light receiving portion which receives light emanated from the optical measuring portion 112. In the present embodiment, for example, a semiconductor laser which emits light whose wavelength is 620 nm can be used as the light source 407. Instead of the semiconductor laser, a semiconductor device, such as a light emitting diode (LED), may be used as the light source 407. Moreover, in the present embodiment, for example, a photodiode can be used as the photoreceiver 408. Instead of the photodiode, a charge coupled device (CCD), a photomultimeter, or the like may be used as the photoreceiver 408.

In the present embodiment, an irradiation and light-receiving wavelength of 620 nm is selected on the assumption that the material to be detected is measured by turbidimetric immunoassay. However, the irradiation and light-receiving wavelength can be suitably selected in accordance with the measuring method and a target to be measured. For example, in a case where the target to be measured is urine, it is yellow due to visible absorption. Therefore, it is preferable that the irradiation and light-receiving wavelength be selected while avoiding the wavelength in such absorption range.

As with the configuration of the conventional measuring apparatus, formed inside the measuring apparatus 300 are: the piston mechanism 404 that is a suction portion which suctions the sample to the sample holding portion 102 of the measuring device 100a; a measuring device detach mechanism 410 which detaches the measuring device 100a from the measuring apparatus 300; a controller 401 including a calculating portion which detects or quantitates the material to be detected which is contained in the test sample based on the emanated light received by the photoreceiver 408; a memory 409 that is a storage portion which stores data regarding a calibration curve showing a correlation between the concentration of the human albumin that is the material to be detected and the intensity of the emanated light received by the photoreceiver 408; a recording portion 411 which records measurement results; a transmitting portion 412 which transmits the measurement results to the outside; a receiving portion 413 which receives analytical results from the outside; and a timer portion 406 which measures an elapsed time. In the present embodiment, the piston mechanism 404 is configured to cause a piston to move forward and backward by a linear stepping motor.

As above, the measuring apparatus 300 according to the present embodiment includes: the measuring device attaching portion 301 to which the measuring device 100a is attached; the light source 407 which emits the light incident on the optical measuring portion 112 of the measuring device 100a; the light receiving portion 408 which receives the light emanated from the optical measuring portion 112; and the controller 401 which detects or quantitates the material to be detected which is contained in the test sample held by the sample holding portion 102 of the measuring device 100a based on the intensity of the light received by the light receiving portion 408.

Moreover, as described above, it is preferable that the measuring apparatus 300 include the suction portion which suctions the test sample to supply the test sample to the sample holding portion 102 of the measuring device 100a attached to the measuring device attaching portion 301. To be specific, to facilitate the measurement of the material to be detected which is contained in test sample, it is preferable that the measuring device 100a include the sample supply port 103 and the suction port 104, and the measuring apparatus 300 include the piston mechanism 404 as the suction portion and cause the piston mechanism 404 to suction the air from the sample holding portion 102 of the measuring device 100a to introduce the test sample through the sample supply port 103 of the measuring device 100a to the sample holding portion 102. With this simple configuration in which the suction port 104 of the measuring device 100a is connected to the measuring device attaching portion 301, and the piston mechanism 404 of the measuring apparatus 300 is driven, it is possible to easily supply the test sample through the sample supply port 103 to the sample holding portion 102 of the measuring device 100a.

The measuring apparatus 300 according to the present embodiment includes the piston mechanism 404 which causes the piston to move forward and backward by the linear stepping motor. However, the present embodiment is not limited to this. For example, instead of the linear stepping motor, the piston may be manually moved forward and backward. One example of a mechanism which causes the piston to manually move forward and backward is a piston mechanism similar to a conventional syringe, dispenser, or the like. Note that forward and backward movements of the piston may be manual or automatic. However, it is preferable to cause the piston to automatically move forward and backward to reduce the burden of the operator.

Moreover, a power source for causing the piston to move forward and backward in the piston mechanism 404 does not have to be the linear stepping motor. A common power source, such as a stepping motor or a direct-current motor, may be used.

The stepping motor is a motor whose rotor rotates at a specific rotation angle in response to one pulse input signal, and can determine the rotation angle of the rotor in accordance with the number of input pulses. Therefore, the stepping motor does not require an encoder for positioning. To be specific, the stepping motor is a motor capable of suitably controlling a movement distance of the piston in accordance with the number of input pulses. Forward and backward movements of the piston by the stepping motor is realized by converting the rotational movement of the rotor of the stepping motor into a translatory movement by, for example, a gear mechanism and a translatory mechanism configured by combining a male screw and a female screw. In order to cause the piston to move forward and backward by using the direct-current motor, for example, the translatory mechanism which converts the rotational movement of the rotor into the translatory movement is required. Moreover, in order to appropriately control the movement distance of the piston, the encoder which detects a rotational position of the rotor is required.

The linear stepping motor incorporates the translatory mechanism configured by combining the male screw and the female screw, and is configured such that a rod-like movable portion thereof carries out the translatory movement in accordance with the number of input pulses. Therefore, since the piston mechanism 404 can be configured by directly coupling the piston to the rod-like movable portion, the piston mechanism 404 can be comparatively simplified in configuration.

Next, a method for measuring the material to be detected which is contained in the test sample by using the measuring device and the measuring apparatus according to Embodiment 1 of the present invention will be explained in reference to FIGS. 4 to 6.

Figure 6:
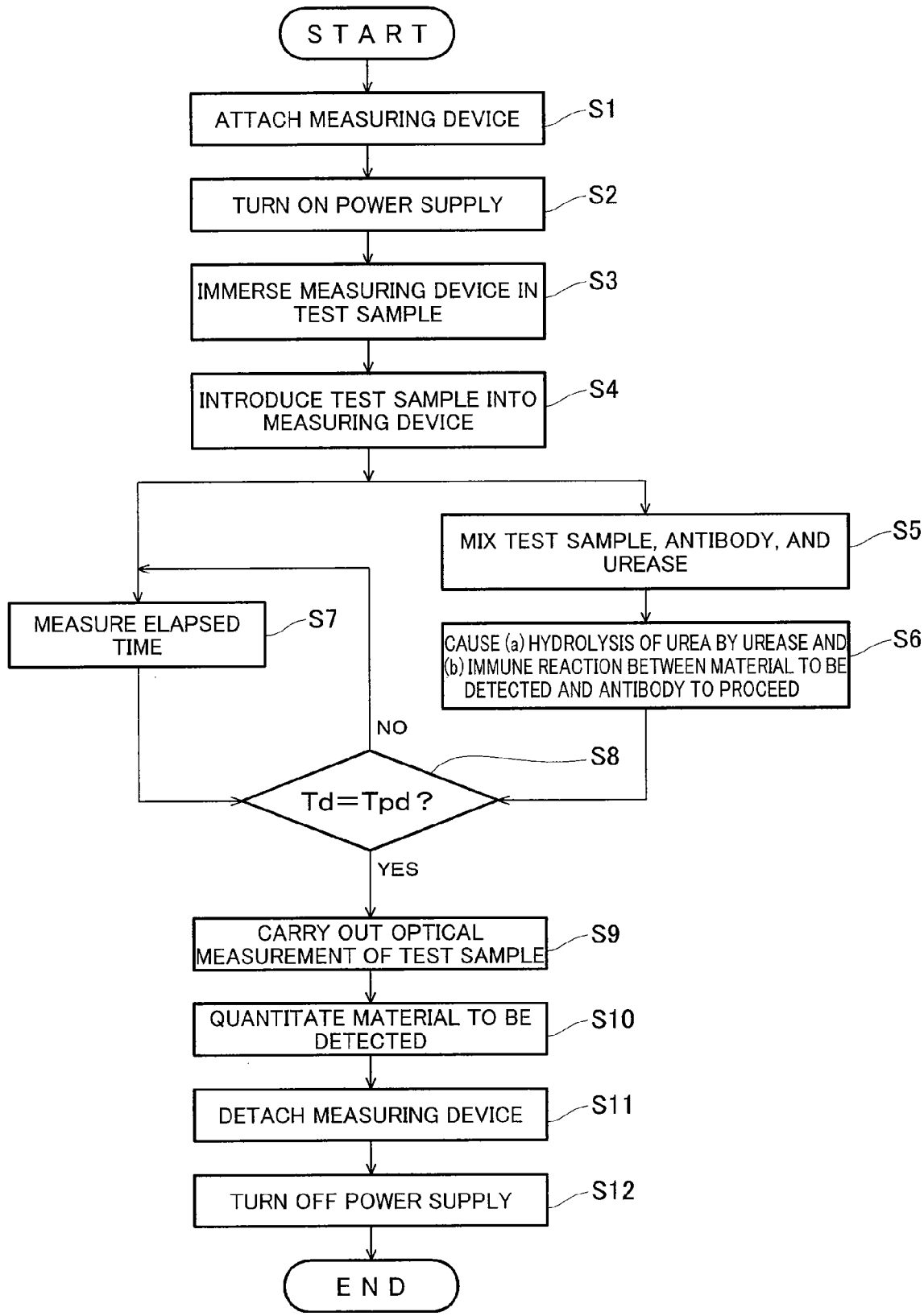
FIG. 6 is a flow chart schematically showing a characteristic operation of the measuring apparatus according to Embodiment 1 of the present invention.

FIG. 6 is a flow chart schematically showing a characteristic operation of the measuring apparatus according to Embodiment 1 of the present invention. For convenience sake, FIG. 6 also shows manipulations by the operator associated with the operations of the measuring apparatus, chemical reactions which proceed in accordance with the manipulations by the operator, and the like.

The operator first causes the suction port 104 of the measuring device 100a to be joined to the device attaching port (not shown) formed inside the measuring device attaching portion 301 of the measuring apparatus 300 to attach the measuring device 100a to the measuring device attaching portion 301 (Step S1).

When the measuring device 100a is attached, a measuring device insertion detecting switch (not shown) that is a micro switch formed inside the measuring device attaching portion 301 is activated in the measuring apparatus 300, so that the controller 401 serving as a control unit detects insertion of the measuring device 100a. Thus, a power supply of the measuring apparatus 300 is turned on (Step S2).

Next, for example, the operator immerses the measuring device 100a in the urine stored in a conveyable container, such as a urine container provided in a toilet bowl or a paper cup, such that at least the sample supply port 103 is immersed in the urine (Step S3).

Next, the operator presses the sample suction start button 303 of the measuring apparatus 300 to activate the piston mechanism 404. With this, the piston provided inside the piston mechanism 404 moves, so that a predetermined amount (3 mL for example) of urine is introduced from the sample supply port 103 of the measuring device 100a into the sample holding portion 102 (Step S4).

Since the test sample is introduced into the sample holding portion 102 of the measuring device 100a, the test sample held by the sample holding portion 102 and the antibody and urease held by the reagent holding portion 111 are mixed with each other (Step S5). Thus, the urine supplied to the sample holding portion 102 dissolves the anti-human albumin antibody and urease that are dry-state reagents held by the first reagent holding portion 109 and the second reagent holding portion 110.

Then, in the sample holding portion 102 of the measuring device 100a, an immune reaction between the human albumin that is the antigen contained in the urine and the anti-human albumin antibody proceeds, and at the same time, the hydrolysis of the urea contained in the urine proceeds by the urease (Step S6). Note that the operator may mix the test sample, the antibody, and the urease by, for example, swinging the measuring apparatus 300 to which the measuring device 100a is attached.

When the test sample is introduced into the sample holding portion 102 of the measuring device 100a in Step S4, the controller 401 of the measuring apparatus 300 activates a timer that is the timer portion 406 to start measuring the elapsed time since the introduction of the test sample into the sample holding portion 102 (Step S7).

Next, when the controller 401 of the measuring apparatus 300 determines in accordance with an output signal of the timer portion 406 that an elapsed time Td since the completion of the supply of the test sample to the sample holding portion 102 has reached a predetermined elapsed time Tpd (two minutes for example) (YES in Step S8), it starts the optical measurement of the test sample held by the sample holding portion 102 of the measuring device 100a (Step S9).

When carrying out the optical measurement of the test sample, the controller 401 of the measuring apparatus 300 causes the light source 407 to irradiate the optical measuring portion 112 of the measuring device 100a with light. Specifically, the controller 401 operates such that the light is emitted from the light source 407 through the light incident portion 107 of the measuring device 100a to the sample holding portion 102, and transmits the urine that is the test sample and scatters by the urine, and the light emanated from the light emanating portion 108 is received by the photoreceiver 408 provided in the measuring apparatus 300 for a predetermined time (three minutes for example).

When the controller 401 of the measuring apparatus 300 determines in accordance with the output signal of the timer portion 406 that the elapsed time Td since the completion of the supply of the test sample to the sample holding portion 102 has not reached the predetermined elapsed time Tpd (NO in Step S8), it operates such that the measurement of the elapsed time Td continues.

Then, the controller 401 of the measuring device 300 reads out the calibration curve which is stored in the memory 409 and shows the correlation between the intensity of the emanated light and the concentration of the human albumin, and refers to this calibration curve, thereby converting the intensity of the emanated light received by the photoreceiver 408 into the concentration of the human albumin. With this, the measuring device 300 quantitates the human albumin that is the material to be detected which is contained in the urine that is the test sample (Step S10).

When the human albumin that is the material to be detected is quantitated in Step S10, the concentration of the human albumin which is obtained by the above quantitation is displayed on the display portion 302 of the measuring device 300. With this, a user of the measuring device 300 can recognize the completion of the measurement of the concentration of the human albumin contained in the urine. At this time, preferably, the concentration of the human albumin which is obtained by the above quantitation is stored in the memory 409 together with the time measured by the timer portion 406.

In accordance with the configuration of the measuring device 300 according to the present embodiment, data regarding the concentration of the human albumin which is obtained by the quantitation can be recorded in a removable recording medium, such as an SD card, by the recording portion 411. With this, since the user can easily take out the measurement results from the measuring device 300, he or she can bring or send by mail the recording medium to a professional analysis company to request detailed analysis of the measurement results.

Moreover, in accordance with the configuration of the measuring device 300 according to the present embodiment, the data regarding the concentration of the human albumin which is obtained by the quantitation can be sent to outside of the measuring device 300 by the sending portion 412. With this, the measurement results can be sent to an analysis related department in a hospital or an analysis related company, and be analyzed by the analysis related department or the analysis related company. Therefore, it is possible to shorten a time elapsing from the measurement to the analysis.

Further, in accordance with the configuration of the measuring device 300 according to the present embodiment, the measuring device 300 includes the receiving portion 413 which receives the analytical result of the analysis related department or the analysis related company. Therefore, the analytical result can be quickly fed back to the user.

Last, when the operator presses the measuring device detach button 304 of the measuring apparatus 300, the measuring device detach mechanism 410 is activated, and the piston inside the piston mechanism 404 moves. With this, the urine held in the sample holding portion 102 of the measuring device 100a is discharged from the sample supply port 103 to a container, such as the toilet bowl or the paper cup, and the measuring device 100a is automatically detached from the measuring apparatus 300 (Step S11).

When the measuring device 100a is detached, the measuring device insertion detecting switch that is the micro switch provided inside the measuring device attaching portion 301 is activated in the measuring apparatus 300, so that the controller 401 detects detachment of the measuring device 100a. With this, the power supply of the measuring apparatus 300 is turned off (Step S12).

The present embodiment shows that the measuring apparatus 300 causes the test sample to be discharged from the measuring device 100a and causes the measuring device 100a to be automatically detached from the measuring apparatus 300. However, the present embodiment is not limited to this. For example, the user may manually detach the measuring device 100a from the measuring device attaching portion 301 without providing a mechanism for realizing the detachment of the measuring device 100a and the discharging of the test sample.

In accordance with the present invention, it is possible to provide the measuring device, the measuring apparatus, and the measuring method, each capable of reducing measurement errors caused by the urea contained in the test sample and quickly and accurately measuring the material to be detected (antigen) that is the target material to be measured, by the simple configuration described as above.

Examples of the test sample in the present embodiment are body fluids, such as serum, blood plasma, urine, interstitial fluid, and lymph fluid, and liquids, such as supernatant liquid of culture medium. Especially, the urine containing the urea is preferable as the test sample since daily health control is noninvasively realized at home. Moreover, a mixture of the body fluid and the reagent, such as enzyme, antibody, or pigment, which reacts with a specific component in the body fluid may be supplied to the measuring device 100a as the test sample.

Moreover, in consideration of a urine qualitative test performed at an initial stage of the health control, a renal function test, a pregnancy test, an ovulation test, and the like, there is a need for measurements of protein, microalbumin, hormones, such as hCG and LH, and the like. For such measurements, the optical measurement based on the antigen-antibody reaction is suitable. Therefore, examples of the material to be detected in the present invention are albumin, hCG, LH, CRP, IgG, and hormones of visceral fat. Moreover, examples of the optical measurement method are methods, such as the nephelometric immunoassay, the turbidimetric immunoassay, and latex agglutination immunoassay, for measuring the turbidity level of the test sample based on the antigen-antibody reaction.

The foregoing has explained one example of the embodiment according to the present invention. However, the shape of the measuring device 100a is not limited to the shape described in the present embodiment. The measuring device 100a may have any shape as long as the shape of the measuring device 100a satisfies constituent features of the present invention, and the effects of the present invention can be obtained.

Hereinafter, the configuration of Modification Example of the measuring device according to the present embodiment will be explained in reference to FIGS. 7 and 8.

Figure 7:
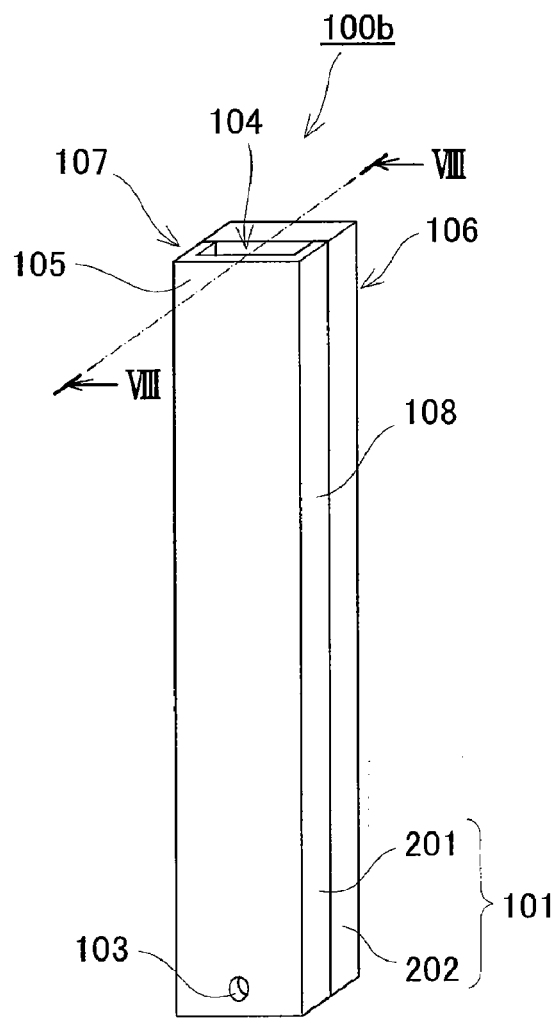
FIG. 7 is a perspective view schematically showing the configuration of Modification Example of the measuring device according to Embodiment 1 of the present invention.

FIG. 7 is a perspective view schematically showing the configuration of Modification Example of the measuring device according to Embodiment 1 of the present invention. FIG. 8 is a cross-sectional view schematically showing the configuration of a cross section taken along line VIII-VIII of Modification Example of the measuring device shown in FIG. 7. In FIGS. 7 and 8, same reference numbers are used for components similar to the components shown in FIGS. 1 and 2, and detailed explanations thereof are omitted.

As shown in FIG. 7, a measuring device 100b as Modification Example of the measuring device 100a according to the present embodiment includes the base body 101 of a bottomed hollow rectangular solid shape having therein a space serving as the sample holding portion 102. Then, the sample supply port 103 is formed at a predetermined position of the first surface 105 of the base body 101.

Figure 8:
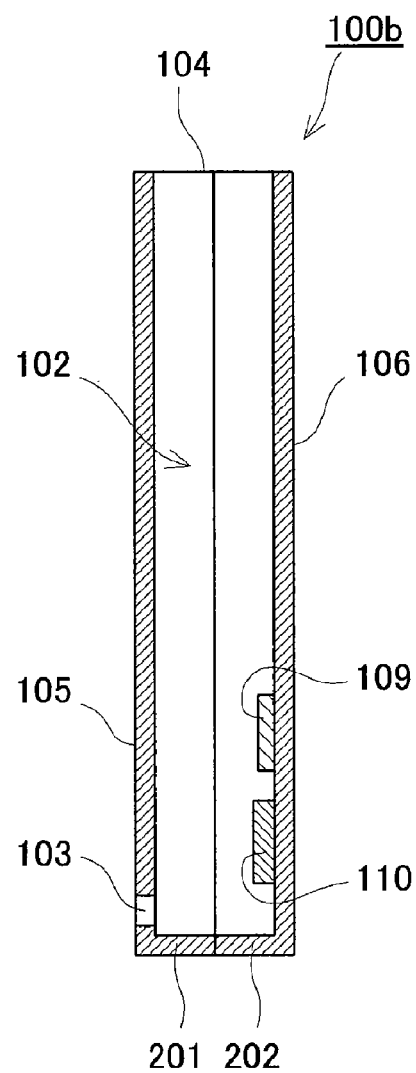
FIG. 8 is a cross-sectional view schematically showing the configuration of a cross section taken along line VIII-VIII of Modification Example of the measuring device shown in FIG. 7.

Moreover, as shown in FIGS. 7 and 8, the base body 101 as Modification Example is constituted by a member (first member 201) having the first surface 105, the second surface 107, the third surface 108, and a bottom portion, and a rear surface plate (second member 202) having the fourth surface 106.

As with the measuring device 100a, the first reagent holding portion 109 and the second reagent holding portion 110 can be formed in the measuring device 100b by applying and drying the aqueous solution containing the reagent for the optical measurement on an inner side of the fourth surface 106. Instead of this, the porous carrier which is made of glass fiber, filter paper, or the like and carries the reagent by being immersed in the reagent solution and then dried or freeze-dried, may be attached to the bottom surface of the concave portion of the second member 202.

Other than this, the measuring device 100b is the same as the measuring device 100a.

Embodiment 2

Hereinafter, another preferred embodiment of the measuring device according to Embodiment 2 of the present invention will be explained in detail.

The present embodiment will explain a case where a urease-antibody complex is obtained by combining in advance the antibody and urease used in Embodiment 1, and the urease-antibody complex is placed in the reagent holding portion.

Figure 9:
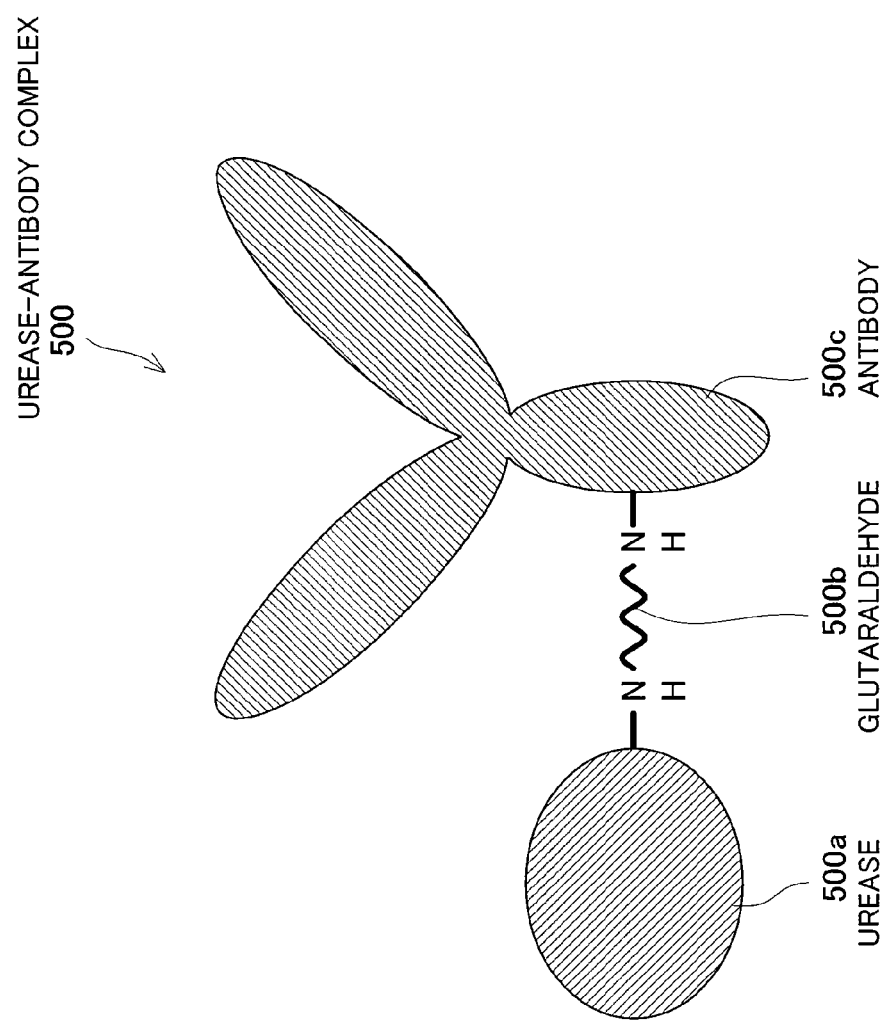
FIG. 9 is a conceptual diagram schematically showing the configuration of a urease-antibody complex used in Embodiment 2 of the present invention.

FIG. 9 is a conceptual diagram schematically showing the configuration of the urease-antibody complex used in Embodiment 2 of the present invention.

As shown in FIG. 9, a urease-antibody complex 500 according to the present embodiment includes urease 500a, glutaraldehyde 500b, and an antibody 500c.

The urease-antibody complex 500 is prepared as below.

That is, a 1 μM antibody aqueous solution (for example, the aqueous solution of the antibody to the human albumin) and a 1 μM urease aqueous solution, which are equal in amount, are mixed with each other, and a glutaraldehyde aqueous solution is added to this mixture solution such that a final concentration becomes 0.25 μM (mole ratio of 2:2:1). By stirring this solution at room temperature for an hour, amino acid residues (for example, lysine) on the surface of the antibody and on the surface of the urease are cross-linked by glutaraldehyde. Thus, the urease-antibody complex 500 is obtained.

As with Embodiment 1, in the present embodiment, a certain amount of the aqueous solution of the urease-antibody complex 500 prepared as above is applied to be dropped on the bottom surface of the concave portion of the second member 202 by using a micro syringe, or the like. Then, the second member 202 is placed at about room temperature to 30° C. to evaporate moisture. Thus, the first reagent holding portion 109 supporting the anti-human albumin antibody in a dry state is formed. For example, 0.7 mL of the aqueous solution of the urease-antibody complex 500 is dropped on the dropped portion whose area is 5 cm². Then, as with Embodiment 1, the measuring device is assembled and completed.

Using the measuring device 100a (measuring device 100b) obtained as above, and the same measuring apparatus 300 and measuring method as in Embodiment 1, a predetermined amount (3 mL for example) of the urine containing the human albumin that is the antigen is suctioned from the sample supply port 103 of the measuring device 100a to the sample holding portion 102. Then, the urine supplied to the sample holding portion 102 of the measuring device 100a dissolves the anti-human albumin antibody-urease complex that is the dry-state reagent held by the first reagent holding portion 109. Thus, as with Embodiment 1, the immune reaction between the human albumin that is the antigen contained in the urine and the anti-human albumin antibody proceeds, and at the same time, the hydrolysis of the urea contained in the urine by the urease proceeds.

The amount of urease supported by the measuring device 100a in the present embodiment is about one fourth of that in Embodiment 1. Regardless of this, changes in quantitative value of the concentration of the human albumin obtained by the method described in Embodiment 1, with respect to changes in concentration of the urea contained in the urine become smaller than those in Embodiment 1. This may be because since the urease is combined with the antibody, the hydrolysis of only the urea located in the vicinity of the antibody can be effectively carried out. As above, by using the antibody with which the urease is combined, the effects of the present invention can be further efficiently obtained.

The present embodiment has described an example in which glutaraldehyde is used as the crosslinking agent when preparing the complex by crosslinking of the antibody and the urease. However, the present embodiment is not limited to this. The other crosslinking agent, such as a compound having an epoxide group or an active ester group at a molecular weight terminal, may be used. Such group reacts with an amino group to form covalent binding. Examples of such compound are polyethylene glycol diglycidyl ether and bis (N-hydroxy succinimidyl) alkyl. Moreover, a compound having a maleimide group, which reacts with a thiol group, at both molecular terminals can realize cross-linking of the antibody and the urease, as with the above. Or, a compound having one functional group, which reacts with the amino group and the thiol group, at each molecular terminal may be used.

EXAMPLE 1

Hereinafter, Examples according to the present invention will be specifically explained while being compared with Comparative Example.

First, Comparative Example will be explained.

COMPARATIVE EXAMPLE 1

In Comparative Example 1, one example of the measurement of the albumin by immune agglutination using the anti-albumin antibody will be explained.

In Comparative Example 1, 0.1 mL of an aqueous solution of 2.66 μM (about 4 mg/mL) of the antibody (anti-albumin antibody) to the human albumin was poured into a cell container made of polystyrene resin. The cell container used in Comparative Example 1 had an external shape of a rectangular solid of 3 cm times 1 cm times 1 cm, and had a hollow portion of a rectangular solid of 2.75 cm times 0.5 cm times 0.5 cm. To be specific, the thickness of the resin forming the cell container was 0.25 cm, and one surface of the rectangular solid of the cell container was open to be communicated with the hollow portion. Then, 0.1 mL of an aqueous solution containing albumin whose concentration was 20 mg/dL and urea of a known concentration was added to the cell container storing the antibody aqueous solution such that the concentration of the albumin became 10 mg/dL, and the concentration of the urea became various predetermined concentrations.

Then, the cell container was vibrated by using a commercially available vibratory stirrer (VORTEX) to strongly stir this mixture solution in the cell container for five seconds. After the stirring, the cell container was placed for 40 seconds to proceed the combining and agglutination between the albumin and the antibody. During this time, a semiconductor laser whose electric power was 1 mW irradiated one surface of the cell container with light whose wavelength was 630 nm. Then, the light incident on the cell container passed through a wall surface of the cell container and was scattered by the aggregate generated by the combining and agglomeration between the albumin and the antibody in the reaction solution, and the scattered light was emanated from the wall surfaces of the cell container having the incident surface and the other surfaces. At this time, the scattered light emanated from the wall surface perpendicular to the light incident surface was measured by using the photodiode.

Figure 10:
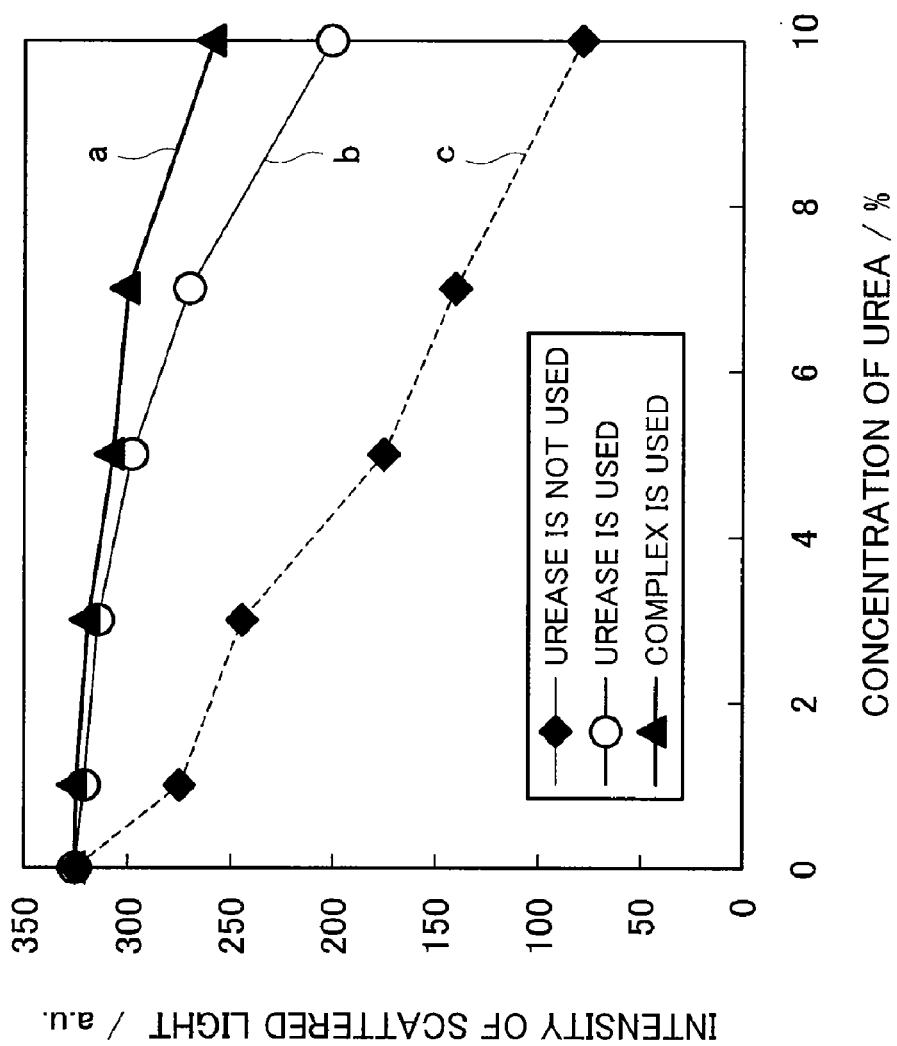
FIG. 10 is a graph schematically showing results of an experiment regarding the influence of the concentration of the urea on the intensity of scattered light.

FIG. 10 is a graph schematically showing results of an experiment regarding the influence of the concentration of the urea on the intensity of the scattered light. In FIG. 10, a curved line a denotes the relation between the intensity of the scattered light and the concentration of the urea in a case where the urease-antibody complex is used, a curved line b denotes the relation between the intensity of the scattered light and the concentration of the urea in a case where only the urease is used, and a curved line c denotes the relation between the intensity of the scattered light and the concentration of the urea in a case where the urease is not used. It is known that the normal concentration of the urea contained in the urine is about 2 to 8%.

Data shown by the curved line c in FIG. 10 is a measurement result showing the relation between the intensity of the scattered light obtained 45 seconds after the mixing of the albumin and the antibody and the concentration of the urea used.

As is clear from the curved line c, in a case where the urease was not used, the intensity of the scattered light significantly decreased as the concentration of the urea increased. Therefore, in accordance with the conventional method for measuring the albumin in Comparative Example 1, it is clear that the intensity of the scattered light is influenced by the urea contained in the test sample, and significant measurement errors corresponding to the concentration of the urea occur in the results of the concentration measurement.

As above, the reason why the measurement of the albumin is influenced by the urea may be because the antibody is denatured by the urea, and this decreases a combining power of the antibody with respect to the antigen (albumin). In addition, the reason why the measurement of the albumin is influenced by the urea may be because the size of the aggregate made of the antibody and the antigen decreases by the decrease in the combining power. The combining power may decrease as the concentration of the urea increases. Thus, the intensity of the scattered light may decrease as the concentration of the urea increases. Or, the generation of the aggregate made of the antibody and the antigen may be disturbed by the existence of the urea, and as a result, the intensity of the scattered light may decrease as the concentration of the urea increases.

EXAMPLE 1

Next, Example 1 will be explained.

Example 1 will explain one example in which in the measurement of the albumin by the immune agglutination using the anti-albumin antibody, the urease was dissolved in a reaction liquid to coexist with the anti-albumin antibody.

In Example 1, the hydrolysis of the urea by the coexisting urease was expected.

In Example 1, 0.1 mL of the aqueous solution containing 2.66 µM (about 4 mg/mL) of the antibody (anti-albumin antibody) to the human albumin and 2.66 µM of the urease was poured into the cell container made of polystyrene resin. The cell container used in Example 1 had an external shape of a rectangular solid of 3 cm times 1 cm times 1 cm, and had a hollow portion of a rectangular solid of 2.75 cm times 0.5 cm times 0.5 cm. To be specific, the thickness of the resin forming the cell container was 0.25 cm, and one surface of the rectangular solid of the cell container was open to be communicated with the hollow portion. Then, 0.1 mL of an aqueous solution containing albumin whose concentration was 20 mg/dL and urea of a known concentration was added to the cell container storing the antibody aqueous solution such that the concentration of the albumin became 10 mg/dL, and the concentration of the urea became various predetermined concentrations.

Then, the cell container was vibrated by using a commercially available vibratory stirrer (VORTEX) to strongly stir the mixture solution in the cell container for five seconds. After the stirring, the cell container was placed for 40 seconds to proceed the combining and agglutination between the albumin and the antibody and the hydrolysis reaction of the urea by the urease. During this time, a semiconductor laser whose electric power was 1 mW irradiated one surface of the cell container with light whose wavelength was 630 nm. Then, the light incident on the cell container passed through a wall surface of the cell container and was scattered by the aggregate generated by the combining and agglomeration between the albumin and the antibody in the reaction solution, and the scattered light was emanated from the wall surfaces of the cell container having the incident surface and the other surfaces. At this time, the scattered light emanated from the wall surface perpendicular to the light incident surface was measured by using the photodiode.

Data shown by the curved line b in FIG. 10 is a measurement result showing the relation between the intensity of the scattered light obtained 45 seconds after the mixing of the albumin, the antibody, and the urease and the concentration of the urea used.

As is clear from the comparison between the curved lines c and b, the decrease in the intensity of the scattered light due to the increase in the concentration of the urea was suppressed by the coexisting urease. Thus, the reason why the measurement result of the intensity of the scattered light is not significantly influenced by the concentration of the urea is because the hydrolysis of the urea is carried out by the coexisting urease, and the degree of denaturalization of the antibody is smaller than the case where the urease does not coexist with the antibody. Moreover, the reason why the measurement result of the intensity of the scattered light is not significantly influenced by the concentration of the urea may be because the decrease in the combining power of the antibody with respect to the antigen (albumin) is comparatively suppressed, and this suppresses the reduction in size of the antibody-antigen aggregate caused due to the decrease in the combining power. Thus, the decrease in the intensity of the scattered light due to the increase in the concentration of the urea may be suppressed as compared to Comparative Example 1. Or, the disturbing of the generation of the antibody-antigen aggregate by the urea may be reduced by the hydrolysis caused by the urease, and as a result, the decrease in the intensity of the scattered light due to the increase in the concentration of the urea may be suppressed as compared to Comparative Example 1.

EXAMPLE 2

Next, Example 2 will be explained.

Example 2 will explain one example in which the albumin was measured by the immune agglutination using the anti-albumin antibody-urease complex.

In Example 2, the effective hydrolysis of the urea by the urease combined and complexed with the antibody was expected.

In Example 2, the urease-antibody complex was prepared as below.

That is, 0.2 mL of an aqueous solution of 2.66 µM (about 4 mg/mL) of the antibody (anti-albumin antibody) to the human albumin and 0.2 mL of a 2.66 µM urease aqueous solution were mixed with each other, and a small amount of a 1 mM glutaraldehyde aqueous solution was added to this mixture solution such that a final concentration became 1.33 µM (mole ratio of 2:2:1). By stirring this mixture solution at room temperature for an hour, amino acid residues (for example, lysine) on the surface of the antibody and on the surface of the urease were cross-linked by glutaraldehyde. Thus, the urease-antibody complex was obtained. Then, in Example 2, 0.1 mL of an aqueous solution of the urease-antibody complex obtained as above was poured into the cell container made of polystyrene resin.

The cell container used in Example 2 had an external shape of a rectangular solid of 3 cm times 1 cm times 1 cm, and had a hollow portion of a rectangular solid of 2.75 cm times 0.5 cm times 0.5 cm. To be specific, the thickness of the resin forming the cell container was 0.25 cm, and one surface of the rectangular solid of the cell container was open to be communicated with the hollow portion. Then, 0.1 mL of an aqueous solution containing albumin whose concentration was 20 mg/dL and urea of a known concentration was added to the cell container storing the aqueous solution of the urease-antibody complex such that the concentration of the albumin became 10 mg/dL, and the concentration of the urea became various predetermined concentrations.

Then, the cell container was vibrated by using a commercially available vibratory stirrer (VORTEX) to strongly stir the mixture solution in the cell container for five seconds. After the stirring, the cell container was placed for 40 seconds to proceed the combining and agglutination between the albumin and the antibody and the hydrolysis reaction of the urea by the urease. During this time, a semiconductor laser whose electric power was 1 mW irradiated one surface of the cell container with light whose wavelength was 630 nm. Then, the light incident on the cell container passed through a wall surface of the cell container and was scattered by the albumin-antibody aggregate in the reaction solution, and the scattered light was emanated from the wall surfaces of the cell container having the incident surface and the other surfaces. At this time, the scattered light emanated from the wall surface perpendicular to the light incident surface was measured by using the photodiode.

Data shown by the curved line a in FIG. 10 is a measurement result showing the relation between the intensity of the scattered light obtained 45 seconds after the mixing of the albumin and the urease-antibody complex and the concentration of the urea used.

As is clear from the comparison among the curved lines a, b, and c, the decrease in the intensity of the scattered light due to the increase in the concentration of the urea was further suppressed as compared to the example (Comparative Example 1) in which the urease did not exist and the example (Example 1) in which the urease was dissolved to coexist with the antibody. Thus, the reason why the measurement result of the intensity of the scattered light is not almost influenced by the concentration of the urea is because the hydrolysis of the urea located around the antibody is efficiently carried out by the urease combined with the antibody, and the degree of denaturalization of the antibody is much smaller than the case where the urease does not coexist with the antibody and the case where the urease is dissolved to coexist with the antibody. Moreover, the reason why the measurement result of the intensity of the scattered light is not almost influenced by the concentration of the urea may be because the decrease in the combining power of the antibody with respect to the antigen (albumin) is further effectively suppressed, and this further suppresses the reduction in size of the antibody-antigen aggregate caused due to the decrease in the combining power. Thus, the decrease in the intensity of the scattered light due to the increase in the concentration of the urea may be further suppressed as compared to Comparative Example 1 and Example 1. Or, the disturbing of the generation of the antibody-antigen aggregate by the urea may be reduced by the hydrolysis caused by the urease combined with the antibody, and as a result, the decrease in the intensity of the scattered light due to the increase in the concentration of the urea may be further suppressed as compared to Comparative Example 1 and Example 1.

Thus, in accordance with Comparative Example 1 and Examples 1 and 2, it was confirmed that the present invention was effective to the measurement of the material to be detected which is contained in the test sample containing the urea.

INDUSTRIAL APPLICABILITY

The measuring device, the measuring apparatus, and the measuring method according to the present invention have industrial applicability as the measuring device, the measuring apparatus, and the measuring method, each having a simple configuration and capable of reducing measurement errors caused by the urea contained in the test sample and accurately measuring the material to be detected. Therefore, the measuring device, the measuring apparatus, and the measuring method according to the present invention is useful in medical and medical related testing fields, especially in a case where measurements are carried out using urine as a test sample.

The invention claimed is:

1. A method of detecting an antigen in a test sample, the method comprising of:
   introducing a test sample into a measuring device, through an inlet of the measuring device,
   wherein the measuring device comprises a reagent,
   the test sample comprises urea and an antigen, and the reagent comprises a conjugate comprising an antibody to the antigen and a urease molecule;
   dissolving the reagent by contacting the reagent with the test sample introduced through the inlet of the measuring device, hydrolyzing the urea with the urease and forming an aggregate of the antigen and the antibody;
   irradiating the measuring device with light;
   measuring the light scattered by the aggregate or light penetrating the test sample; and
   detecting the antigen with a turbidimetric immunoassay based on the measured light.

2. The method according to claim 1, wherein the introducing step includes:
   immersing the inlet of the measuring device in the test sample; and
   suctioning the test sample from the inlet into the measuring device.

* * * * *